US012728034B2

(12) United States Patent
Smith et al.

(10) Patent No.: US 12,728,034 B2
(45) Date of Patent: Sep. 8, 2026

(54) ALGORITHM USING COMMON PATIENT PARAMETERS TO DETERMINE CORRECT PAD SIZE

(71) Applicant: C. R. Bard, Inc., Franklin Lakes, NJ (US)

(72) Inventors: Jesse Smith, Broomfield, CO (US); Niharika Pathare, Thane (IN); Gabriel A. Johnston, Broomfield, CO (US); Mengjia Yi, Westminster, CO (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 188 days.

(21) Appl. No.: 18/282,748

(22) PCT Filed: Mar. 16, 2022

(86) PCT No.: PCT/US2022/020633

§ 371 (c)(1),
(2) Date: Sep. 18, 2023

(87) PCT Pub. No.: WO2022/197858

PCT Pub. Date: Sep. 22, 2022

(65) Prior Publication Data

US 2024/0173165 A1 May 30, 2024

Related U.S. Application Data

(60) Provisional application No. 63/162,955, filed on Mar. 18, 2021.

(51) Int. Cl.
*A61F 7/08* (2006.01)
*A61F 7/00* (2006.01)
(Continued)

(52) U.S. Cl.
CPC .............. *A61F 7/08* (2013.01); *A61F 7/0085* (2013.01); *G16H 10/60* (2018.01); *G16H 20/30* (2018.01);
(Continued)

(58) Field of Classification Search
CPC .. A61F 7/08; A61F 7/0085; A61F 2007/0018; A61F 2007/0041;
(Continued)

(56) References Cited

U.S. PATENT DOCUMENTS 3,064,649 A 11/1962 Fuson
3,830,676 A 8/1974 Elkins
(Continued)

FOREIGN PATENT DOCUMENTS

AU 2007201161 B2 12/2010
CA 2882654 C 6/2017
(Continued)

OTHER PUBLICATIONS

PCT/US2022/050498 filed Nov. 18, 2022 International Search Report and Written Opinion dated Jun. 20, 2023.
(Continued)

*Primary Examiner* — Beverly M Flanagan
(74) *Attorney, Agent, or Firm* — Rutan & Tucker LLP

(57) ABSTRACT

A system is disclosed for recommending a thermal pad set for use in providing a targeted temperature management (TTM) therapy to a patient, where the system includes a computer implemented method. The computer implemented method includes receiving a request for a thermal pad set recommendation from a clinician device, receiving a patient's identification from the clinician device, retrieving one or more patient parameter values from an electronic medical record for the patient, determining a pad set recommendation according to the patient parameter values in
(Continued)

combination with a pad set correlation table, and displaying the pad set recommendation on the clinician device. Also disclosed herein is a system including a non-transitory computer-readable medium with instructions encoded thereon and one or more processors configured to, when executing the instructions, perform operations in accordance with processes of the computer implemented method.

18 Claims, 6 Drawing Sheets

(51) Int. Cl.
*G16H 10/60* (2018.01)
*G16H 20/30* (2018.01)
*G16H 50/70* (2018.01)

(52) U.S. Cl.
CPC ...... *G16H 50/70* (2018.01); *A61F 2007/0018* (2013.01); *A61F 2007/0041* (2013.01); *A61F 2007/0054* (2013.01)

(58) Field of Classification Search
CPC ............ A61F 2007/0054; G16H 20/30; G61H 10/60; G61H 50/70
USPC .......................................................... 607/104
See application file for complete search history.

(56) References Cited

U.S. PATENT DOCUMENTS 3,846,518 A 11/1974 McPhee
3,944,261 A 3/1976 Reed et al.
4,149,541 A 4/1979 Gammons et al.
4,181,132 A 1/1980 Parks
4,231,425 A 11/1980 Engstrom
4,256,692 A 3/1981 Cover
4,298,006 A 11/1981 Parks
4,416,280 A 11/1983 Carpenter et al.
4,459,468 A 7/1984 Bailey
4,476,867 A 10/1984 Parks
4,497,324 A 2/1985 Sullivan et al.
4,596,571 A 6/1986 Bellotti et al.
4,844,072 A 7/1989 French et al.
4,894,164 A 1/1990 Polaschegg
4,901,734 A 2/1990 Griffin et al.
4,961,422 A 10/1990 Marchosky et al.
D319,312 S 8/1991 Schneider
5,086,771 A 2/1992 Molloy
5,097,829 A 3/1992 Quisenberry
5,195,531 A 3/1993 Bennett
5,241,951 A 9/1993 Mason et al.
5,266,778 A 11/1993 Bailey
5,378,230 A 1/1995 Mahurkar
5,383,919 A 1/1995 Kelly et al.
5,385,529 A 1/1995 Koch
5,411,541 A 5/1995 Bell et al.
5,464,042 A 11/1995 Haunhorst
5,472,417 A 12/1995 Martin et al.
5,494,074 A 2/1996 Ramacier, Jr. et al.
5,496,357 A 3/1996 Jensen et al.
5,542,916 A 8/1996 Hirsch et al.
5,568,946 A 10/1996 Jackowski
5,591,220 A 1/1997 Mahawili
5,609,620 A 3/1997 Daily
5,626,129 A 5/1997 Klimm et al.
5,713,941 A 2/1998 Robins et al.
5,730,720 A 3/1998 Sites et al.
5,733,319 A 3/1998 Neilson et al.
5,785,716 A 7/1998 Bayron et al.
5,845,943 A 12/1998 Ramacier, Jr. et al.
5,862,803 A 1/1999 Besson et al.
5,868,433 A 2/1999 Matkovich
5,871,526 A 2/1999 Gibbs et al.
5,881,410 A 3/1999 Yamada
5,897,142 A 4/1999 Kulevsky
5,928,273 A 7/1999 Schmidt
5,948,012 A 9/1999 Mahaffey et al.
6,125,636 A 10/2000 Taylor et al.
6,141,572 A 10/2000 Haas
6,149,670 A 11/2000 Worthen et al.
6,149,674 A 11/2000 Borders
6,188,930 B1 2/2001 Carson
6,197,045 B1 3/2001 Carson
6,198,394 B1 3/2001 Jacobsen et al.
6,231,594 B1 5/2001 Dae
6,238,354 B1 5/2001 Alvarez
6,290,717 B1 9/2001 Philips
6,375,674 B1 4/2002 Carson
6,432,124 B1 8/2002 Worthen et al.
6,436,130 B1 8/2002 Philips et al.
6,454,792 B1 9/2002 Noda et al.
6,454,793 B1 9/2002 Evans et al.
6,461,379 B1 10/2002 Carson et al.
6,500,200 B1 12/2002 Kushnir
6,517,510 B1 2/2003 Stewart et al.
6,520,933 B1 2/2003 Evans et al.
6,551,348 B1 4/2003 Blalock et al.
6,582,457 B2 6/2003 Dae et al.
6,592,612 B1 7/2003 Samson et al.
6,609,732 B1 8/2003 Souvatzidis et al.
6,620,187 B2 9/2003 Carson et al.
6,620,188 B1 9/2003 Ginsburg et al.
6,620,189 B1 9/2003 Machold et al.
6,645,232 B2 11/2003 Carson
6,648,905 B2 11/2003 Hoglund et al.
6,660,027 B2 12/2003 Gruszecki et al.
6,669,715 B2 12/2003 Hoglund et al.
6,682,551 B1 1/2004 Worthen et al.
6,692,285 B2 2/2004 Islam
6,692,518 B2 2/2004 Carson
6,699,267 B2 3/2004 Voorhees et al.
6,702,839 B1 3/2004 Dae et al.
6,726,710 B2 4/2004 Worthen et al.
6,799,063 B2 9/2004 Carson
6,802,855 B2 10/2004 Ellingboe et al.
6,818,012 B2 11/2004 Ellingboe
6,827,728 B2 12/2004 Ellingboe et al.
6,827,898 B1 12/2004 Fausset et al.
6,871,878 B2 3/2005 Miros
6,887,263 B2 5/2005 Bleam et al.
6,921,198 B2 7/2005 Gruszecki et al.
7,008,444 B2 3/2006 Dae et al.
7,077,858 B2 7/2006 Fletcher et al.
7,089,995 B2 8/2006 Koscheyev et al.
7,179,279 B2 2/2007 Radons et al.
7,198,093 B1 4/2007 Elkins
7,207,986 B2 4/2007 Abboud et al.
7,211,104 B2 5/2007 Edelman
7,241,307 B2 7/2007 Lennox
7,294,112 B1 11/2007 Dunlop
7,361,186 B2 4/2008 Voorhees et al.
7,434,842 B2 10/2008 Schmidt
D595,845 S 7/2009 Mros et al.
D601,248 S 9/2009 Mros et al.
7,666,213 B2 2/2010 Freedman, Jr. et al.
7,704,220 B2 4/2010 Solar et al.
7,827,815 B2 11/2010 Carson et al.
7,867,266 B2 1/2011 Collins
7,914,563 B2 3/2011 Mason et al.
8,047,010 B2 11/2011 Carson et al.
D652,510 S 1/2012 Lombardi, III et al.
8,092,415 B2 1/2012 Moehle et al.
8,182,520 B2 5/2012 Schock et al.
8,221,389 B2 7/2012 Brenner et al.
8,449,589 B1 5/2013 Harsy
8,539,948 B2 9/2013 Ionascu et al.
8,596,688 B2 12/2013 Pisula, Jr. et al.
8,597,217 B2 12/2013 Lowe et al.
8,622,980 B2 1/2014 Zinn
8,647,374 B2 2/2014 Koewler
8,663,106 B2 3/2014 Stivoric et al.
8,683,996 B2 4/2014 Allen et al.

(56) References Cited

U.S. PATENT DOCUMENTS 8,808,344 B2 8/2014 Scott et al.
8,911,485 B2 12/2014 Brian, III et al.
D730,518 S 5/2015 Lombardi, III et al.
9,119,705 B2 9/2015 Parish et al.
9,278,024 B2 3/2016 Scott et al.
9,283,109 B2 3/2016 Guyuron et al.
9,314,367 B2 4/2016 Callister et al.
D757,259 S 5/2016 Duck et al.
9,402,763 B2 8/2016 Bledsoe
9,439,803 B2 9/2016 Varga et al.
9,566,185 B2 2/2017 Carson et al.
9,763,823 B2 9/2017 Voorhees et al.
9,918,502 B2 3/2018 Oliver et al.
10,123,902 B2 11/2018 Carson et al.
10,390,992 B2 8/2019 Hopper et al.
10,441,707 B2 10/2019 Voorhees et al.
10,471,247 B2 11/2019 Kellner et al.
10,588,779 B2 3/2020 Voorhees et al.
10,632,321 B2 4/2020 Schwarz et al.
10,677,688 B2 6/2020 Rivas et al.
11,013,635 B2 5/2021 Schirrmacher et al.
11,039,952 B2 6/2021 Paxman et al.
11,058,572 B2 7/2021 Kostic et al.
11,285,039 B2 3/2022 Steele et al.
11,311,414 B2 4/2022 Scott et al.
12,109,146 B1 10/2024 Stefanoff
12,340,881 B2 * 6/2025 Kramb .................. G16H 10/60
2002/0058974 A1 5/2002 Van Duren et al.
2002/0091308 A1 7/2002 Kipshidze et al.
2002/0096311 A1 7/2002 Kushnir et al.
2002/0165590 A1 11/2002 Crowe et al.
2003/0078639 A1 4/2003 Carson
2003/0092975 A1 5/2003 Casscells et al.
2003/0163183 A1 8/2003 Carson
2004/0030373 A1 2/2004 Ellingboe et al.
2004/0059212 A1 3/2004 Abreu
2004/0064169 A1 4/2004 Briscoe et al.
2004/0073280 A1 4/2004 Dae et al.
2004/0087606 A1 5/2004 Voorhees et al.
2004/0122559 A1 6/2004 Young et al.
2004/0143170 A1 7/2004 DuRousseau
2004/0170409 A1 9/2004 Faries et al.
2004/0210166 A1 10/2004 Soh et al.
2004/0225341 A1 11/2004 Schock et al.
2005/0020958 A1 1/2005 Paolini et al.
2005/0065583 A1 3/2005 Voorhees et al.
2005/0143797 A1 6/2005 Parish et al.
2005/0177212 A1 8/2005 Njemanze
2005/0234532 A1 10/2005 Eggers et al.
2006/0069418 A1 3/2006 Schock et al.
2006/0122673 A1 6/2006 Callister et al.
2006/0177343 A1 8/2006 Brian et al.
2006/0190062 A1 8/2006 Worthen
2006/0190066 A1 8/2006 Worthen
2006/0260699 A1 11/2006 Edelman et al.
2006/0293732 A1 12/2006 Collins et al.
2006/0293734 A1 12/2006 Scott et al.
2007/0063850 A1 3/2007 Devaul et al.
2007/0118054 A1 5/2007 Pinhas et al.
2007/0118194 A1 5/2007 Mason et al.
2007/0129622 A1 6/2007 Bourget et al.
2007/0173705 A1 7/2007 Teller et al.
2007/0173735 A1 7/2007 Callister et al.
2007/0191918 A1 8/2007 MacHold et al.
2007/0213793 A1 9/2007 Hayes
2007/0236012 A1 10/2007 Kerin et al.
2008/0071150 A1 3/2008 Miesel et al.
2008/0167535 A1 7/2008 Stivoric et al.
2008/0255637 A1 10/2008 Oishi
2008/0307822 A1 12/2008 Richardson
2009/0018504 A1 1/2009 Pile-Spellman et al.
2009/0018626 A1 1/2009 Levinson et al.
2009/0018627 A1 1/2009 Levinson et al.
2009/0033333 A1 2/2009 Gribova et al.
2009/0093748 A1 4/2009 Patterson et al.
2009/0099629 A1 4/2009 Carson et al.
2009/0112298 A1 4/2009 Jusiak et al.
2009/0131835 A1 5/2009 Voorhees et al.
2009/0149779 A1 6/2009 Russo et al.
2009/0182400 A1 7/2009 Dae et al.
2009/0237264 A1 9/2009 Bobey et al.
2009/0312676 A1 12/2009 Rousso et al.
2009/0312823 A1 12/2009 Patience et al.
2010/0087900 A1 4/2010 Flint
2010/0100090 A1 4/2010 Rose
2010/0152822 A1 6/2010 Callister et al.
2010/0191165 A1 7/2010 Appling et al.
2010/0204765 A1 8/2010 Hall et al.
2011/0046693 A1 2/2011 Lee et al.
2011/0061838 A1 3/2011 Richardson
2011/0152982 A1 6/2011 Richardson
2011/0166884 A1 7/2011 Lesselroth et al.
2011/0238050 A1 9/2011 Allison et al.
2011/0319754 A1 12/2011 Solar et al.
2012/0029408 A1 2/2012 Beaudin
2012/0095536 A1 4/2012 Machold et al.
2013/0046366 A1 2/2013 Ross, III et al.
2013/0116758 A1 5/2013 Levinson et al.
2013/0138185 A1 5/2013 Paxman et al.
2013/0238042 A1 9/2013 Gildersleeve et al.
2013/0324964 A1 12/2013 Florescu
2014/0046411 A1 2/2014 Elkins et al.
2014/0094881 A1 4/2014 Dabrowiak et al.
2014/0172050 A1 6/2014 Dabrowiak
2014/0249466 A1 9/2014 Hakim
2014/0343639 A1 11/2014 Hopper et al.
2015/0018667 A1 1/2015 Radman et al.
2015/0025411 A1 1/2015 Callister et al.
2015/0051673 A1 2/2015 Rivas Tapia
2015/0223972 A1 8/2015 Dabrowiak
2015/0230973 A1 8/2015 Dabrowiak et al.
2015/0250643 A1 9/2015 Paradis
2015/0335467 A1 11/2015 Varga et al.
2015/0335468 A1 11/2015 Rose et al.
2016/0022477 A1 1/2016 Schaefer et al.
2016/0058613 A1 3/2016 Palazzolo et al.
2016/0287433 A1 10/2016 Mazzone
2016/0361196 A1 12/2016 Spence et al.
2017/0049618 A1 2/2017 Ward et al.
2017/0071783 A1 3/2017 Calderon
2017/0135855 A1 5/2017 Stefan et al.
2017/0151087 A1 6/2017 Carson et al.
2017/0224528 A1 8/2017 Berg et al.
2017/0224529 A1 8/2017 Berg et al.
2017/0246029 A1 8/2017 Clark
2017/0246374 A1 8/2017 Voorhees et al.
2017/0259035 A1 9/2017 Smith et al.
2017/0348144 A1 12/2017 Taylor et al.
2017/0348145 A1 12/2017 Voorhees et al.
2017/0354534 A1 12/2017 Paradis et al.
2018/0042762 A1 2/2018 Galer
2018/0140459 A1 5/2018 Taylor et al.
2018/0147086 A1 5/2018 Evans et al.
2018/0163907 A1 6/2018 Brugger et al.
2018/0207024 A1 7/2018 Dabrowiak et al.
2018/0214302 A1 8/2018 Dabrowiak et al.
2018/0264222 A1 9/2018 Dantanarayana et al.
2019/0073632 A1 * 3/2019 Laster .................... G16H 20/40
2019/0117446 A1 4/2019 Carson et al.
2019/0192337 A1 6/2019 Taylor et al.
2019/0223409 A1 * 7/2019 Godfrey .................... A61F 7/08
2019/0262169 A1 8/2019 Vergara et al.
2020/0000252 A1 1/2020 Wang
2020/0086033 A1 3/2020 Voorhees et al.
2020/0129325 A1 4/2020 Sinha et al.
2020/0158275 A1 5/2020 Whitney, Jr. et al.
2020/0214880 A1 7/2020 Voorhees et al.
2020/0246180 A1 8/2020 Liang et al.
2020/0261261 A1 8/2020 Hopper et al.
2020/0275859 A1 9/2020 Srinivasan
2020/0282197 A1 9/2020 Langer et al.
2020/0289361 A1 9/2020 Tian et al.
2020/0345538 A1 11/2020 Carson et al.
2020/0352781 A1 11/2020 Yang

(56) References Cited

U.S. PATENT DOCUMENTS

| | | | |
|---|---|---|---|
| 2020/0383825 | A1 | 12/2020 | Diller et al. |
| 2021/0022914 | A1 | 1/2021 | Badawi et al. |
| 2021/0059854 | A1 | 3/2021 | Yazawa et al. |
| 2021/0060230 | A1 | 3/2021 | Hopper et al. |
| 2023/0405205 | A1 | 12/2023 | Voorhees et al. |
| 2024/0082050 | A1 | 3/2024 | Johnston et al. |
| 2024/0148952 | A1 | 5/2024 | Hoglund et al. |
| 2025/0127655 | A1 | 4/2025 | McKinnon et al. |
| 2025/0161106 | A1 | 5/2025 | Johnston et al. |
| 2025/0177196 | A1 | 6/2025 | Bartolovitch et al. |

FOREIGN PATENT DOCUMENTS

| | | | | |
|---|---|---|---|---|
| CN | 111643256 | A | 9/2020 | |
| CN | 114712091 | A | 7/2022 | |
| DE | 2851602 | A1 | 6/1980 | |
| DE | 19531935 | A1 | 2/1997 | |
| EP | 0322225 | A2 | 6/1989 | |
| EP | 0757907 | A1 | 2/1997 | |
| EP | 0846440 | A2 | 6/1998 | |
| EP | 1059903 | B1 | 12/2004 | |
| EP | 2269527 | A1 | 1/2011 | |
| EP | 2471574 | A1 | 7/2012 | |
| GB | 1604955 | A | 12/1981 | |
| GB | 2350566 | A | 12/2000 | |
| JP | 2005518837 | A | 6/2005 | |
| JP | 2008528129 | A | 7/2008 | |
| JP | 2011500174 | A | 1/2011 | |
| WO | 9636950 | A1 | 11/1996 | |
| WO | 9706840 | A1 | 2/1997 | |
| WO | 03030790 | A1 | 4/2003 | |
| WO | 03066137 | A1 | 8/2003 | |
| WO | 03071999 | A1 | 9/2003 | |
| WO | 2005117546 | A2 | 12/2005 | |
| WO | 2006034877 | A1 | 4/2006 | |
| WO | 2006081288 | A2 | 8/2006 | |
| WO | 2007121480 | A2 | 10/2007 | |
| WO | 2009049297 | A1 | 4/2009 | |
| WO | 2013102056 | A1 | 7/2013 | |
| WO | 2014189941 | A1 | 11/2014 | |
| WO | 2017035341 | A1 | 3/2017 | |
| WO | 2017172837 | A1 | 10/2017 | |
| WO | WO-2019133232 | A1 * | 7/2019 | ............... A61F 7/08 |
| WO | 2021139913 | A1 | 7/2021 | |
| WO | 2021242892 | A1 | 12/2021 | |
| WO | 2022164906 | A1 | 8/2022 | |
| WO | 2022192282 | A1 | 9/2022 | |
| WO | 2022197858 | A1 | 9/2022 | |
| WO | 2022235695 | A1 | 11/2022 | |
| WO | 2023101677 | A1 | 6/2023 | |
| WO | 2023163714 | A1 | 8/2023 | |
| WO | 2023204796 | A1 | 10/2023 | |
| WO | 2024107208 | A1 | 5/2024 | |

OTHER PUBLICATIONS

U.S. Appl. No. 17/735,984, filed May 3, 2022 Board Decision dated Mar. 21, 2025.

U.S. Appl. No. 17/735,984, filed May 3, 2022 Non-Final Office Action dated May 30, 2025.

U.S. Appl. No. 17/922,584, filed Oct. 31, 2022 Non-Final Office Action dated Apr. 23, 2025.

U.S. Appl. No. 17/923,813, filed Nov. 7, 2022 Restriction Requirement dated Mar. 11, 2025.

Baldwin B.A. et al: "Autonomic thermoregulatory effects of electrical stimulation of the hypothalamus in the sheet (Ovis aries)", Journal of Thermal Biology, Pergamon Press, Oxford, GB, vol. 9, No. 4, Oct. 1, 1984, pp. 279-284.

Bard Access Systems, Inc., Additional Instructions for Use of Power-Trialysis* Aphacurve* Short-Term Dialysis Catheter, Apr. 2012, C.R. Bard Inc., Salt Lake City, Utah.

Bard Access Systems, Inc., Flow Performance Guidelines for Bard Access Systems Power-Trialysis* Alphacurve* Short-Term Dialysis Catheter, Apr. 2012, C.R. Bard Inc., Salt Lake City, Utah.

Bard Access Systems, Inc., Power-Trialysis* Short-Term Dialysis Catheter Overview and Features, www.bardaccess.com/dial-power-trialysis.php, May 19, 2014, C.R. Bard Inc., Salt Lake City, Utah.

Bard Access Systems, Inc., Short-Term Dialysis Catheter Instructions for Use, Power-Trialysis Short-Term Dialysis Catheter, Mar. 2009, C.R. Bard Inc., Salt Lake City, Utah.

Christoph Testori, et al., Rapid Induction of Mild Therapeutic Hypothermia by Extracorporeal Veno-Venous Blood Cooling in Humans, Resuscitation, 2013, vol. 84, pp. 1051-1055, Elsevier Ireland Ltd.

Michael Sung, et al., Shiver Motion and Core Body Temperature Classification for Wearable Soldier Health Monitoring Systems, MIT Media Laboratory, Human Dynamics Group, 4 Pages. Nov. 2004.

PCT/US2021/031837 filed May 11, 2021 International Search Report and Written Opinion dated Aug. 30, 2021.

PCT/US2021/034308 filed May 26, 2021 International Search Report and Written Opinion dated Aug. 26, 2021.

PCT/US2022/020633 filed Mar. 16, 2022 International Search Report and Written Opinion dated May 23, 2022.

PCT/US2022/027508 filed May 3, 2022 International Search Report and Written Opinion dated Sep. 29, 2022.

PCTUS2022013904 filed Jan. 26, 2022 International Search Report and Written Opinion dated Apr. 21, 2022.

Stuart D.G. et al: "Activation and suppression of shivering during septal and hypothalamic stimulation", Experimental Neurology, Elsevier, Amsterdam, NL, vol. 4, No. 6, Dec. 1, 1961, pp. 485-506.

UCSF Department of Radiology & Biomedical Imaging, Vascular Access and Use of Central Lines and Ports in Adults, https://radiology.ucsf.edu/patient-care/patient-safety/contrast/iodinated-/vascular-access-adults, May 15, 2014, The Regents of the University of California, San Francisco, California.

U.S. Appl. No. 16/189,055, filed Nov. 13, 2018 Corrected Notice of Allowance dated May 12, 2020.

U.S. Appl. No. 16/189,055, filed Nov. 13, 2018 Notice of Allowance dated Mar. 13, 2020.

U.S. Appl. No. 16/597,376, filed Oct. 9, 2019 Non-Final Office Action dated Dec. 28, 2022.

U.S. Appl. No. 16/597,376, filed Oct. 9, 2019 Notice of Allowance dated Apr. 24, 2023.

U.S. Appl. No. 16/597,376, filed Oct. 9, 2019 Restriction Requirement dated Sep. 27, 2022.

U.S. Appl. No. 16/820,328, filed Mar. 16, 2020 Notice of Allowance datd May 18, 2022.

U.S. Appl. No. 16/933,710, filed Jul. 20, 2020 Notice of Allowance dated Feb. 23, 2023.

U.S. Appl. No. 17/313,771, filed May 6, 2021 Non-Final Office Action dated Aug. 24, 2021.

U.S. Appl. No. 17/313,771, filed May 6, 2021 Notice of Allowance dated Jan. 18, 2022.

U.S. Appl. No. 17/735,984, filed May 3, 2022 Examiner's Answer dated Aug. 2, 2023.

U.S. Appl. No. 17/735,984, filed May 3, 2022 Final Office Action dated Oct. 20, 2022.

U.S. Appl. No. 17/735,984, filed May 3, 2022 Non-Final Office Action dated Jul. 6, 2022.

Hirchika Imoto et al., "Use of a Peltier chip with a newly devised local brain-cooling system for neocortical seizures in the rat", J Neurosurg 104: 150-156, 2006.

Natalia Mejia et al., "An On-Site Thermoelectric Cooling Device for Cryotherapy and Control of Skin Blood Flow", Journal of Medical Devices vol. 9, pp. 044502-1 to 044502-6, Dec. 2015.

PCT/US2021/061642 filed Dec. 2, 2021 Interantional Search Report and Written Opinion dated Sep. 16, 2022.

PCT/US2022/018008 filed Feb. 25, 2022 International Search Report and Written Opinion dated Oct. 4, 2022.

PCT/US2022/025222 filed Apr. 18, 2022 International Search Report and Written Opinion dated Jan. 30, 2023.

(56) References Cited

OTHER PUBLICATIONS

Shahriar Ahmed et al., "Development of a Cooling Unit for the Emergency Treatment of Head Injury", IFMBE, vol. 14, SpringerLink Conference paper pp. 3243-3246, World Congress on Medical Physics and Biomedical Engineering 2006.
Tauchi et al., "Targeted Temperature Management: Peltier's Element-Based Focal Brain Cooling Protects Penumbra Neurons from Progressive Damage in Experimental Cerebral Ischemia", Therapeutic Hypothermia and Temperature Management, vol. 8, No. 4, 2018.
"Hyperthermia in Cancer Treatment"—National Cancer Institute pp. 1-3 Oct. 30, 2018.
Baronzio G. et al. "A Brief Overview of Hyperthermia in Cancer Treatment"—Journal of Integrative Oncology vol. 3 Issue 1 (2014).
Bull J. "Whole Body Hyperthermia as an Anticancer Agent" CA-A Cancer Journal For Clinician vol. 32, No. 2 pp. 123-128 Mar./Apr. 1982.
Chang et al. "Laparoscopic Continuous Hyperthermic Peritoneal Perfusion" American College of Surgeons vol. 193, No. 2, Aug. 2001 pp. 225-229.
Datta, N.R. et al. "Local hyperthermia combined with radiotherapy and-/or chemotherapy: Recent advances and promises for the future"—Cancer Treatment Reviews 41 pp. 742-753 (2015).
Hildebrandt et al. "The cellular and molecular basis of hyperthermia" Critical Reviews in Oncology/Hematology 43 pp. 33-56 (2002).
Huang et al. "It's Getting Hot in Here: Targeting Cancer Stem-like Cells with Hyperthermia"—Journal of Stem Cell and Transplantation Biology Published Date: Dec. 29, 2017.
Januszewski et al. "Hyperthermia in cancer: is it coming of age?" Lancet Oncology vol. 15 pp. 565-566 May 2014.
Mallory et al. "Therapeutic hyperthermia: The old, the new, and the upcoming" Critical Reviews in Oncology/Hematology 97 (2016) pp. 56-64.
McDaniel et al. "Actively targeting solid tumours with thermoresponsive drug delivery systems that respond to mild hyperthermia" Int Journal Hyperthermia, 2013; 29(6): pp. 501-510.
Oei et al. "Targeting therapy-resistant cancer stem cells by hyperthermia" International Journal of Hyperthermia 33:4, pp. 419-427 (2017).
PCT/US2022/019376 filed Mar. 8, 2022, Internation Search Report and Written Opinion dated Jul. 18, 2022.
Szasz et al. "Local Hyperthermia in Oncology—To Choose or not to Choose?" InTech publication pp. 1-83 (2013).
Van der Zee, J. "Heating the patient: a promising approach?" Annuals of Oncology 13 pp. 1172-1184 (2002).
U.S. Appl. No. 17/735,984, filed May 3, 2022 Final Office Action dated Dec. 5, 2025.
U.S. Appl. No. 17/922,584, filed Oct. 31, 2022 Advisory Action dated Oct. 7, 2025.
U.S. Appl. No. 17/922,584, filed Oct. 31, 2022 Final Office Action dated Aug. 5, 2025.
U.S. Appl. No. 17/922,584, filed Oct. 31, 2022 Non-Final Office Action dated Nov. 4, 2025.
U.S. Appl. No. 17/923,813, filed Nov. 7, 2022 Non-Final Office Action dated Jul. 1, 2025.
U.S. Appl. No. 18/274,415, filed Jul. 26, 2023 Restriction Requirement dated Dec. 5, 2025.
U.S. Appl. No. 18/280,176, filed Sep. 1, 2023 Non-Final Office Action dated Dec. 2, 2025.
U.S. Appl. No. 18/280,176, filed Sep. 1, 2023 Restriction Requirement dated Aug. 25, 2025.
U.S. Appl. No. 17/735,984, filed May 3, 2022 Advisory Action dated Mar. 5, 2026.
U.S. Appl. No. 17/735,984, filed May 3, 2022 Final Office Action dated Apr. 1, 2026.
U.S. Appl. No. 17/923,813, filed Nov. 7, 2022 Advisory Action dated Mar. 2, 2026.
U.S. Appl. No. 17/923,813, filed Nov. 7, 2022 Non-Final Office Action dated Apr. 27, 2026.
U.S. Appl. No. 18/241,775, filed Sep. 1, 2023 Notice of Allowance dated Apr. 24, 2026.
U.S. Appl. No. 18/274,415, filed Jul. 26, 2023 Non-Final Office Action dated Feb. 24, 2026.
US 18/280, 176 filed Sep. 1, 2023 Final Office Action dated Apr. 7, 2026.
U.S. Appl. No. 18/715,064, filed May 30, 2024 Non-Final Office Action dated Mar. 4, 2026.
U.S. Appl. No. 18/844,807, filed Sep. 6, 2024 Restriction Requirement dated Apr. 21, 2026.

* cited by examiner

THERMAL PAD SET CORRELATION TABLE

| THERMAL PAD SET | PATIENT PARAMETERS | | | | | |
|---|---|---|---|---|---|---|
| | WEIGHT RANGE (KG) | HEIGHT RANGE (CM) | BODY FAT (%) | PANT WAIST RANGE (CM) | PANT INSEAM RANGE (CM) | SHOE SIZE RANGE (US) |
| NEONATAL | 1.8 - 4.5 | 40 - 44 | | | | |
| SMALL CHILD | 2.5 - 5 | 44 - 55 | | | | |
| MEDIUM CHILD | 5 - 10 | 55 - 75 | 5 - 40 | 24-33 | 25 - 35 | 4 - 6 |
| LARGE CHILD | 10 - 16 | 75 - 100 | 5 - 40 | 33 - 44 | 35 - 45 | 5 - 7 |
| XX-SMALL ADULT | 16 - 30 | 100 - 125 | 5 - 40 | 44 - 53 | 45 - 55 | 6 - 9 |
| X-SMALL ADULT | 30 - 45 | 125 - 150 | 5 - 40 | 53 - 62 | 55 - 64 | 7 - 10 |
| SMALL ADULT | 45 - 60 | 150 - 165 | 5 - 40 | 62 - 70 | 64 - 73 | 8 - 11 |
| MEDIUM ADULT | 60 - 75 | 165 - 180 | 5 - 40 | 70 - 80 | 73 - 82 | 10 - 12 |
| LARGE ADULT | 75 - 100 | 180 - 205 | 5 - 40 | 80 - 90 | 82 - 93 | 12 - 14 |
| X-LARGE ADULT | >100 | 180 - 205 | 5 - 40 | 90 - 150 | 82 - 93 | 13 - 18 |

FIG. 4

THERMAL PAD SET RECOMMENDATION FORM

| | | |
|---|---|---|
| PATIENT'S NAME | JANE DOE | |
| MALE/FEMALE | F | F/M |
| WEIGHT | 55 | KG |
| HEIGHT | 175 | CM |
| PANT WAIST | 60 | CM |
| PANT INSEAM | 75 | CM |
| SHOE SIZE | 8.5 | US |
| BODY FAT | 15 | % |

RECOMMENDED PAD SET SMALL ADULT

AVAILABLE

ALTERNATIVE RECOMMENDED PAD SET N/A

ALGORITHM USING COMMON PATIENT PARAMETERS TO DETERMINE CORRECT PAD SIZE

PRIORITY

This application is a U.S. national stage application of International Application No. PCT/US2022/020633, filed Mar. 16, 2022, which claims the benefit of priority to U.S. Provisional Application No. 63/162,955 filed Mar. 18, 2021, each of which is incorporated by reference in its entirety into this application.

BACKGROUND

The effect of temperature on the human body has been well documented and the use of targeted temperature management (TTM) systems for selectively cooling and/or heating bodily tissue is known. Elevated temperatures, or hyperthermia, may be harmful to the brain under normal conditions, and even more importantly, during periods of physical stress, such as illness or surgery. Conversely, lower body temperatures, or mild hypothermia, may offer some degree of neuroprotection. Moderate to severe hypothermia tends to be more detrimental to the body, particularly the cardiovascular system.

Targeted temperature management can be viewed in two different aspects. The first aspect of temperature management includes treating abnormal body temperatures, i.e., cooling the body under conditions of hyperthermia or warming the body under conditions of hypothermia. The second aspect of thermoregulation is an evolving treatment that employs techniques that physically control a patient's temperature to provide a physiological benefit, such as cooling a stroke patient to gain some degree of neuroprotection. By way of example, TTM systems may be utilized in early stroke therapy to reduce neurological damage incurred by stroke and head trauma patients. Additional applications include selective patient heating/cooling during surgical procedures such as cardiopulmonary bypass operations.

TTM systems circulate a fluid (e.g., water) through one or more thermal contact pads coupled with a patient to affect surface-to-surface thermal energy exchange with the patient. In general, TTM systems comprise a TTM fluid control module coupled with at least one contact pad via a fluid deliver line. One such TTM system is disclosed in U.S. Pat. No. 6,645,232, titled "Patient Temperature Control System with Fluid Pressure Maintenance" filed Oct. 11, 2001 and one such thermal contact pad and related system is disclosed in U.S. Pat. No. 6,197,045 titled "Cooling/heating Pad and System" filed Jan. 4, 1999, both of which are incorporated herein by reference in their entireties. As noted in the '045 patent, the ability to establish and maintain thermally intimate pad-to-patient contact is of importance to fully realizing medical efficacies with TTM systems.

In some instances, multiple thermal pad sizes are available to accommodate a wide range of patient sizes. To maximize thermal energy exchange with the patient, it may be advantageous to match the thermal pad size to the patient size. As a patient size may be defined by different characteristics such as weight and height, choosing the thermal pad size may require combining the different patient size characteristics is a specific manner to arrive at the optimal pad size. Furthermore, the optimal pad size may not be readily available, in which case the optimal second choice pad size may need to be used. Disclosed here are systems and method for choosing the optimal thermal pad size for a given patient from an available inventory of the thermal pads.

SUMMARY OF THE INVENTION

Briefly summarized, disclosed herein is a system and computerized method for automatically determining a recommended thermal pad set for use in providing a targeted temperature management (TTM) therapy to a patient. In one embodiment, the computerized method includes receiving a request for a thermal pad set recommendation for an identified patient from a clinician device, receiving a patient's identification from the clinician device, accessing an electronic medical record (EMR) for the patient, retrieving one or more patient parameter values from the EMR, determining a pad set recommendation according to the patient parameter values in combination with a pad set correlation table, and displaying the pad set recommendation on the clinician device.

In some embodiments, the pad set includes at least one torso pad and the pad set may also include at least one thigh pad. The patient parameters may include at least two of the patient's gender, weight, height, or body fat percentage. In some embodiments, the patient parameters include at least three of the patient's gender, weight, height, or body fat percentage. Additionally, in some embodiments, the patient parameters may include a plurality of predetermined body shapes, where each body shape may correspond to body measurement ranges or body fat percentage ranges that are used by the computerized in providing a thermal pad set recommendation. Additionally, or alternatively, each body shape may correspond to expected locations for body fat deposits, which may influence the thermal pad set recommendation provided by the computerized method. For example, a patient with a "pear-shaped" body may be expected to have a greater accumulation of body fat around the patient's waist and hip regions than a patient with an "inverted-triangle-shaped" body.

The computerized method may further include receiving one or more other patient parameters from the clinician device and the other patient parameters may include at least one of the patient's pant waist size, pant inseam size, or shoe size. In some embodiments, the other patient parameters include at least two of the patient's pant waist size, pant inseam size, or shoe size.

In some embodiments, determining the pad set recommendation includes determining an initial pad set recommendation in accordance with a first set of patient parameters and determining a refined pad set recommendation in accordance with a second set of patient parameters in combination with the first set of patient parameters. In such embodiments, rendering the pad set recommendation on the clinician device includes rendering refined pad set recommendation. In some embodiments, the refined pad set recommendation is different from the initial pad set recommendation.

The first set of patient parameters may include one or more of the patient parameters, and the second set of patient parameters may include one or more of the other patient parameters. The first set may include the patient's weight and/or the patient's height and the second set of patient parameters may include the patient's pant waist size and/or the patient's pant inseam size.

The computerized method may further include accessing a facility inventory system and determining an availability of the recommended pad set in inventory. In some embodiments, if the pad set is not available in inventory, the computer implemented method further includes determining an alternative pad set and displaying the alternative pad set on the clinician device.

The computerized method may also include determining the recommended thermal pad set according to the patient parameter values using a trained machine learning model, where the trained machine learning model receives as input the one or more patient parameter values and provides one or more resultant scores, and where a highest resultant score is provided as the recommended thermal pad set.

Also disclosed herein is a system including one or more processors and a non-transitory computer-readable medium communicatively coupled to the one or more processors and having instructions stored thereon that, when executed by the one or more processors, cause performance of operations in accordance with processes of the computerized method summarized above.

Also disclosed herein is a non-transitory computer-readable storage medium (CRM) including executable instructions that when executed by one or more processors causes the one or more processors to perform operations in accordance with processes of the computerized method summarized above.

These and other features of the concepts provided herein will become more apparent to those of skill in the art in view of the accompanying drawings and the following description, which describe particular embodiments of such concepts in greater detail.

BRIEF DESCRIPTION OF DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 3 is a block diagram of a system architecture adapted to support a thermal pad set recommendation system, in accordance with some embodiments.

FIG. 4 is a thermal pad set correlation table of the thermal pad set recommendation system of FIG. 3, in accordance with some embodiments.

FIG. 5 is a screen shot of a thermal pad set recommendation form of the thermal pad set recommendation system, in accordance with some embodiments.

FIG. 6 is flow chart for a process of determining the thermal pad set recommendation, in accordance with some embodiments.

DETAILED DESCRIPTION

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

The phrases “connected to” and “coupled with” refer to any form of interaction between two or more entities, including mechanical, electrical, magnetic, electromagnetic, fluid, signal, communicative (including wireless), and thermal interaction. Two components may be connected to or coupled with each other even though they are not in direct contact with each other. For example, two components may be coupled with each other through an intermediate component.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Unless defined otherwise, all technical and scientific terms used herein have the same meaning as commonly understood by those of ordinary skill in the art.

Figure 1:
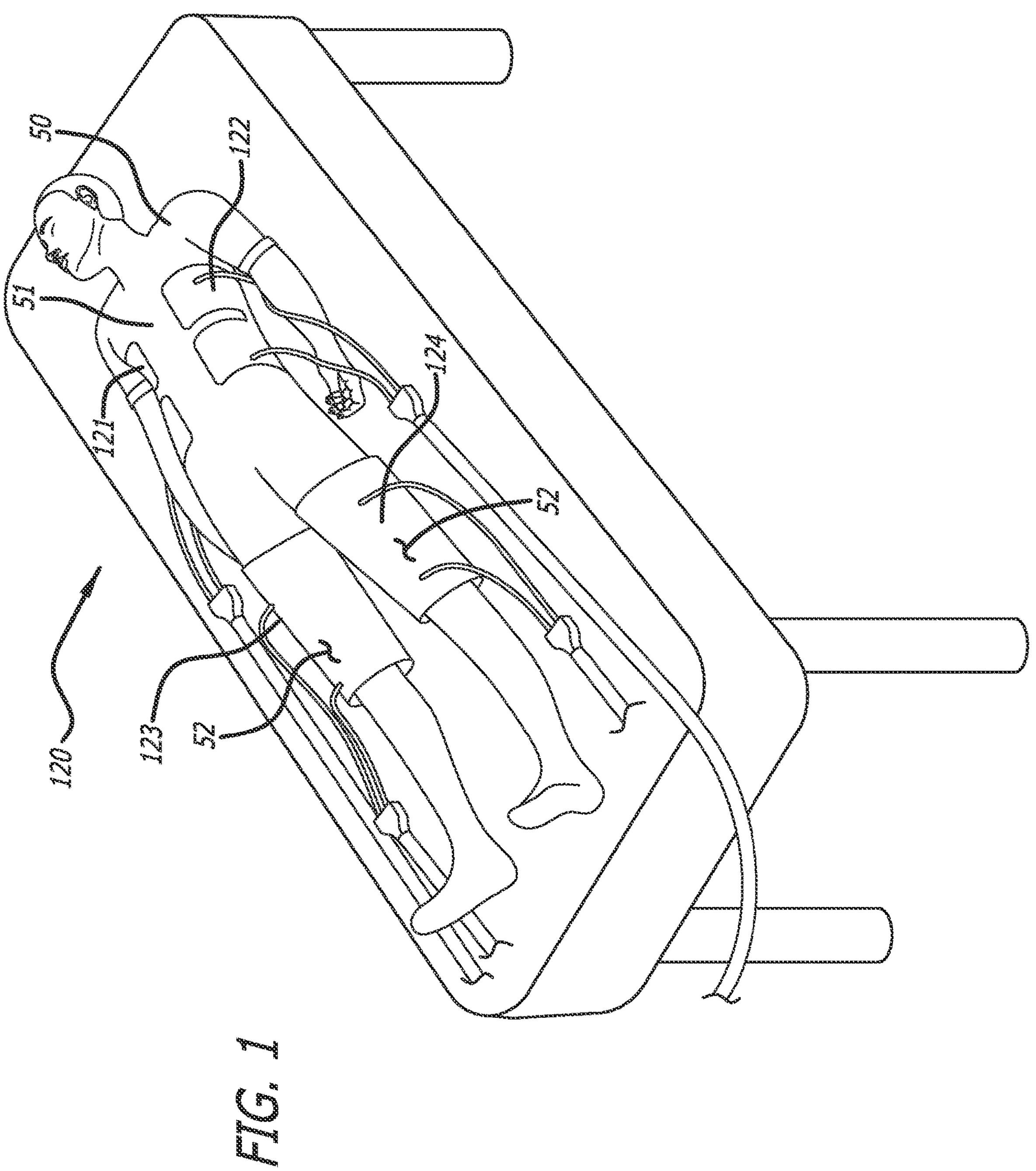
FIG. 1 illustrates a patient undergoing a targeted temperature management (TTM) therapy, in accordance with some embodiments.

FIG. 1 illustrates a patient 50 undergoing a targeted temperature management (TTM) therapy, in accordance with some embodiments. In the illustrated embodiment, a thermal contact pad set 120 including four thermal contact pads 121, 122, 123, and 124 are applied to the patient 50. Torso pads 121 and 122 are applied to the torso 51 of the patient 50 such that each torso pad 121, 122 extends partially around the torso 51 of the patient 50. Thigh pads 123 and 124 are individually applied to each thigh 52 of the patient 50 such that each thigh pad 121, 122 extends at least partially around the thigh 52 of the patient 50. While the illustrated embodiment of the pad set 120 includes four pads, other embodiments may include one, two, three, four, five, six, or more thermal contact pads.

As shown, the pads are sized to cover a specified portion of the patient. For example, the torso pads may extend from the waist to the breast of the patient 50. Similarly, the thigh pads may extend from the groin area to the knee of the patient. As described below, different pad sets 120 may include pads of different sizes (i.e., dimensions) to accommodate different patient sizes.

Figure 2:
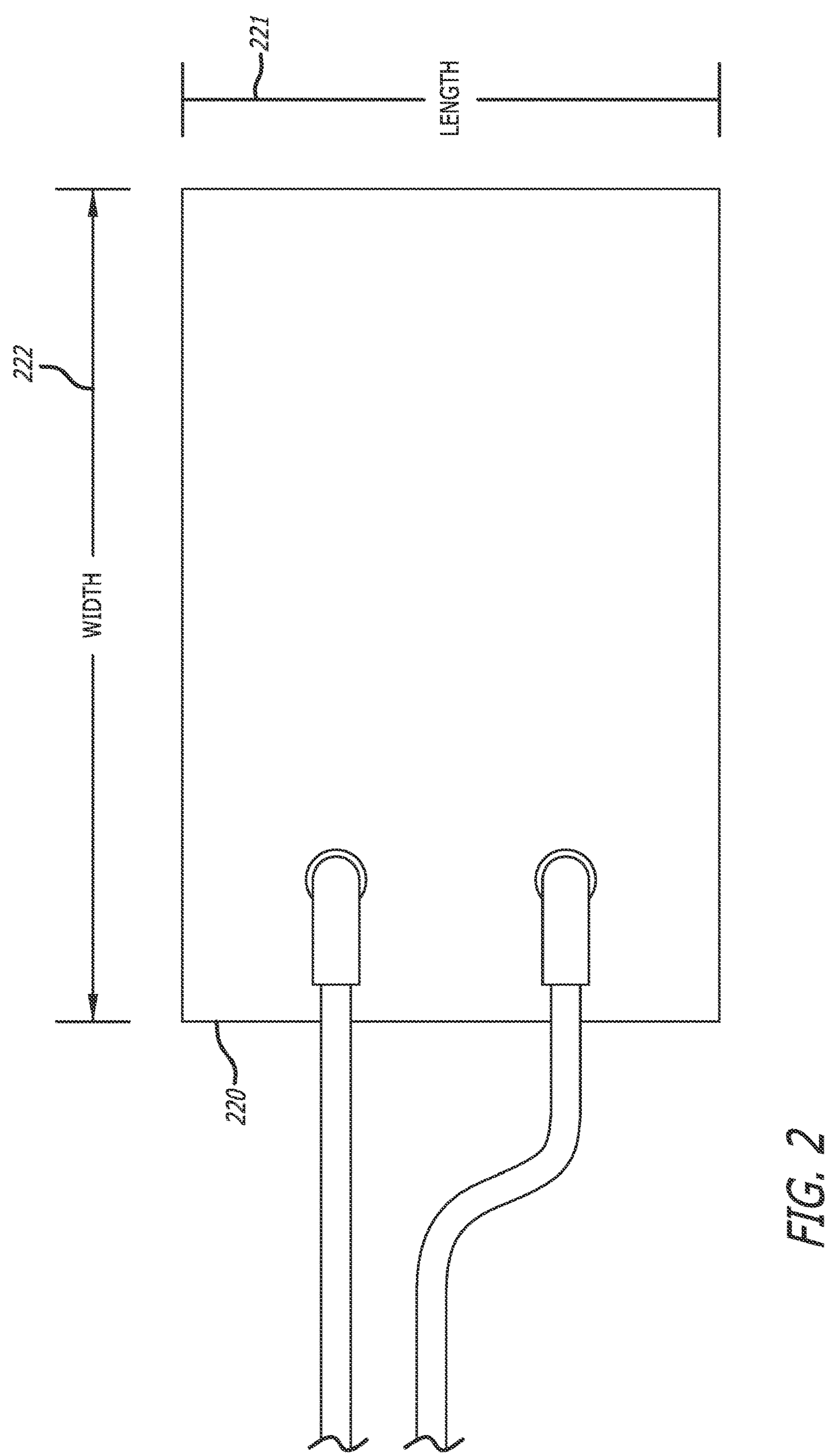
FIG. 2 is a top view of a thermal pad of a TTM system, in accordance with some embodiments.

FIG. 2 is a top view of a thermal pad 220 which may be representative of any one pad of the pad set 120. In some embodiments, the thermal pad 220 may generally define a rectangular shape. As shown, the pad 220 defines a length dimension 221 which in use may be oriented parallel to a height of the patient 50. The pad 220 similarly defines a width 222 which may extend at least partially around a portion of the patient 50. In the illustrated embodiment, the length 221 and the width 222 may substantially define a fit for the pad 220 on the patient 50. For example, in the case of the thigh pads 123, 124, the length 221 may extend along a thigh length of the patient 50, i.e., between the groin area and the knee of the patient 50, and further in the case of the thigh pads 123, 124, the width 222 may extend partially or completely along a circumference of the thigh of the patient 50, i.e., around the thigh 52 of the patient 50. In some instances, the width 222 may exceed a circumference of the thigh 52 so that end portions of the width 222 may overlap each other. It should be understood that the rectangular shape of the pad 220 is not intended to be limiting and merely provides one illustrative embodiment. A pad as disclosed herein may take various shapes.

In the case of the torso pads 121, 122, the length 221 may extend along a length of the torso 51, i.e., from the breast of the patient 50 to a waist or hips of the patient 50. Similarly, the width 222 of the torso pad 121, 122 may extend partially around the torso 51 of the patient 50, i.e., extend along a portion of a torso circumference of the patient 50. As illustrated in FIG. 1, the torso pads 121, 122 may be positioned end to end such that the widths 222 of the torso pads 121, 122 extend around opposite portions of the torso 51. As such, when combined, the pads 121, 122 may extend substantially along the torso circumference of the patient 50. In some instances, the combined widths 222 of the torso pads 121, 122 may exceed the circumference of the torso 51 so that end portions of the torso pads 121, 122 may overlap each other.

In the illustrated embodiment, the length 221 and the width 222 may substantially define a fit for the pad 220 on the patient 50. As such, pads 220 of different lengths 221 and widths 222 may be provided to define the fit for patients 50 of different sizes. As patient sizes may range from neonates to extra-large adults, multiple pad sets 120 may be defined for use across the range of patient sizes. In use, the clinician may select a pad set 120 to fit a specific patient. While it may be possible for the clinician to obtain direct measurements of the patient 50 when selecting a pad size, obtaining direct measurements, e.g., thigh length or torso circumference, may be awkward or not logically feasible. In some instances, it may be necessary for the clinician to select a pad set 120 without having direct access to the patient 50.

In some instances, the clinician may select a pad set 120 in accordance with one or more available patient parameter values, e.g., a weight and/or height of the patient 50. However, as may be appreciated by one of ordinary skill, the patient dimensions that correlate with thermal pad dimensions may vary across patients having the same weight or height. For example, two patients having the same weight, may have different torso lengths or torso circumferences. As such, it may be advantageous for clinician to utilize a tool to more accurately select a pad set 120 in accordance with available patient parameter values.

Figure 3:
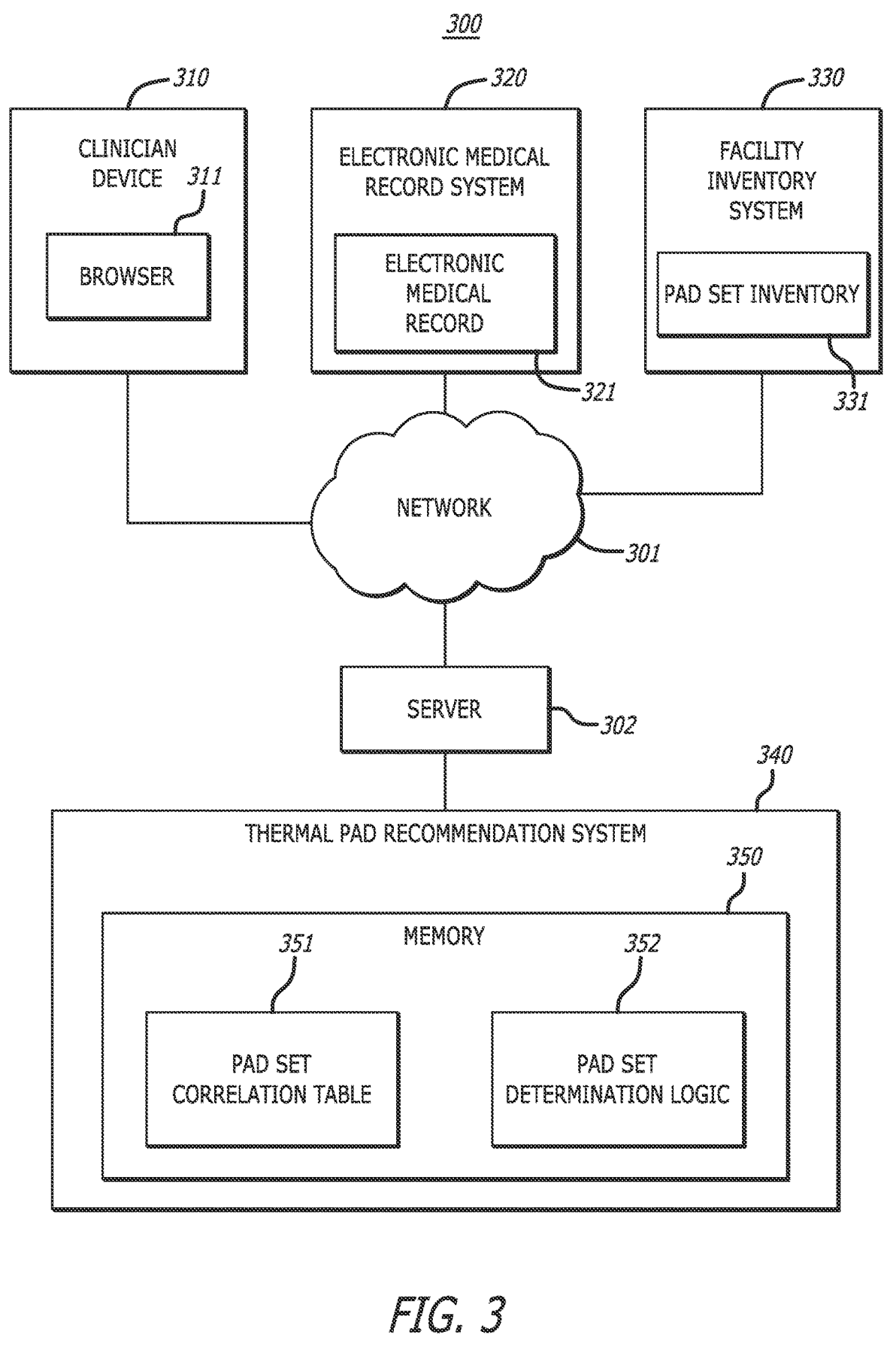

FIG. 3 illustrates a system architecture 300 adapted to support one embodiment of a thermal pad recommendation system (system) 340. The network 301 represents the communication pathways between the clinician device 310 and the system 340. In one embodiment, the network 301 is the Internet. The network can also utilize dedicated or private communication links (e.g., WAN, MAN, or LAN) that are not necessarily part of the Internet. The network uses standard communications technologies and/or protocols.

The server 302 may be a web server configured to present web pages or other web content, which form the basic interface to the clinician device 310. The clinician uses the clinician device 310 to access one or more web pages, and provide data to the pad recommendation system 340. In the context of this application, "data" is understood to include information about the patient 50, the pad set 120, a pad set inventory, and the like. For example, for information related to the patient 50, the data can include information such as weight, height, body fat percentage, pant waist size, pant inseam size, shoe size and the like. Also, for information about the pad set 120, the data can include the number of pads, types of pads, pad dimensions, part numbers, and the like.

The clinician device 310 is used by the clinician for interacting with the system 340. The clinician device 310 can be any device that is or incorporates a computer such as a personal computer (PC), a desktop computer, a laptop computer, a notebook, a smartphone, or the like. A computer is a device having one or more general or special purpose processors, memory, storage, and networking components (either wired or wireless). The device executes an operating system, for example, a Microsoft Windows-compatible operating system (OS), Apple OS X or iOS, a Linux distribution, or Google's Android OS. In some embodiments, the clinician device 310 may use a web browser 311, such as Microsoft Internet Explorer, Mozilla Firefox, Google Chrome, Apple Safari and/or Opera, as an interface to interact with the system 340. The clinician may provide patient parameter data to the system 340 by directly inputting values for defined patient parameters for the patient 50 via the clinician device 310.

The system architecture 300 may include access to an electronic medical record (EMR) system 320. The EMR system 320 may include an electronic medical record (EMR) 321 for the patient 50 and the EMR 321 may include one or more patient parameters. The patient parameters of the EMR 321 may include the patient's weight, the patient's height, and the patient's body-fat percentage. In some embodiments, the one or more patient parameters may be associated with an identifier or other key that may be provided on a patient wristband (e.g., a hospital wristband), a patient chart, etc. As one example, the identifier may be a barcode that is printed on the patient wristband or a patient chart such that scanning of the barcode provides at least a subset of the one or more patient parameters as input to the thermal pad recommendation system 340. The clinician device may include a barcode scanner or utilize a software application where execution thereof results in the scanning of the barcode. For instance, when the clinician device 310 includes a computer, the barcode scanner may be a peripheral device that couples to the laptop and may be considered an aspect of the clinician device 310. In other instances, such as when the clinician device 310 is a mobile device (e.g., phone or tablet), the clinician device 310 may include a software application (logic) that, upon execution, performs operations including scanning the barcode. In either instance, upon receiving the scanned barcode, the clinician device 310 may access the one or more patient parameters that are associated with the barcode and provide such to the thermal pad recommendation system 340.

The system architecture 300 may include access to a facility inventory system 330. The inventory system 330 may include a pad set inventory 331 defining a current availability within the facility of any one pad set 120 of a catalog of pad sets 120. In some instances, a pad selected from inventory may be relayed to the thermal pad recommendation system 340 and to the pad set determination logic 352, which as discussed below, may utilize machine learning techniques (or other artificial intelligence techniques) to determine a thermal pad size recommendation. Further, the size of the selected pad may be utilized in updating or refining the pad set determination logic 352 in order to improve accuracy of future recommendations. For example, the size of the selected pad may be utilized in re-training a machine learning model of the pad set determination logic 352.

In use, the clinician device 310 issues a request to the system 340 to obtain a recommendation for the pad set 120 to be used with a specified patient 50. In response, the system 340 provides a recommendation to the client 310 regarding the pad set 120 to be used with the specified patient 50 when performing the TTM therapy based on available patient parameter values. In some embodiments, the system 340 may also provide an alternative pad set recommendation.

Those of skill in the art will appreciate that the system architecture 300 may contain other modules that are not described herein. In addition, conventional elements, such as firewalls, authentication systems, payment processing systems, network management tools, load balancers, and so forth are not shown as they are not material to the invention. The system 340 may be implemented using a single computer, or a network of computers, including cloud-based computer implementations. The computers are preferably server class computers including one or more high-performance CPUs and 1G or more of main memory, and running an operating system such as LINUX or variants thereof. The operations of the system 111 as described herein can be controlled through either hardware or through computer programs installed in non-transitory computer storage and executed by the processors to perform the functions described herein. The system architecture 300 includes other hardware elements necessary for the operations described here, including network interfaces and protocols, input devices for data entry, and output devices for display, printing, or other presentations of data.

The system 340 includes a non-transitory computer readable storage medium 350 having a pad set correlation table 351 and a pad set determination logic 352 stored thereon, the logic 352 including a pad set determination algorithm. The pad set correlation table 351 associates value ranges of defined patient parameters with corresponding pad sets 120 as described in relation to FIG. 4. The pad determination logic 352 includes instructions such that when executed by one or more processors is configured to perform operations in accordance with providing the pad set recommendation to the clinician device 310 as further described below. In some embodiments, the non-transitory computer readable storage medium 350 may include multiple pad set correlation tables 351 for different genders. In other embodiments, data for all genders may be included in a single pad set correlation table 351.

In some embodiments, the system architecture 300 may include or have access to a three-dimensional (3D) body scanner (not shown) from which the system 340 may acquire one or more patient parameter values.

In some embodiments, a clinician may utilize a network device that includes a camera (e.g., a mobile phone or a tablet) and capture one or more images of the patient in lieu of an image captured by a 3D body scanner. In such embodiments, logic of the thermal pad recommendation system 340 may use computer-vision techniques to detect the patient and detect certain components of the patient's environment, such as a bed. In some embodiments, the environment components may include a device having specified length, such as a meter stick. Based on the detection of the patient and one or more environment components, the logic may determine dimensions of the patient such as an overall length of the patient body, the length of various portions of the patient body (e.g., length of torso, length arms, lengths of legs, etc.) and a width of various portions of the patient body.

In some embodiments, the pad set determination logic 352 may utilize machine learning techniques (or other artificial intelligence techniques) to determine a thermal pad size recommendation. For example, a machine learning model may be trained utilizing previously stored data indicating patient dimensions (e.g., manually entered height, weight, shoe size, body measurements, gender, etc., and/or captured images via a 3D body scanner or other cameras), corresponding selected thermal pad sizes and scores as to how the selected thermal pad size fit the patient. Thus, the trained machine learning model may be deployed by the thermal pad recommendation system to score various thermal pad sizes for data indicating patient dimensions, where a highest resultant score may indicate the recommendation.

FIG. 4 illustrates an exemplary pad set correlation table 351. The table 351 includes multiple pads sets 120 defined by sizes ranging from a neonatal size to an extra-large adult size. The table includes value ranges for defined patient parameters that correlate with each pad set 120. For example, as shown in the table 351, the "small adult" pad set 120 correlates typically to patients having a weight between 30 and 45 kg.

In some embodiments, the value ranges of the patient parameters represent typical value ranges for patients 50 across the patient parameters. For example, referring to the table 351, a patient having a weight between 30 and 45 kg may typically have a height between 155 and 165 cm, a body fat percentage between 5 and 40 percent, a pant waist size between 53 and 62 cm, a pant inseam between 64 and 73 cm, and a shoe size between 8 and 11 (US).

In some instances, actual patient parameter values may vary from the typical parameter value ranges in the table 351. For example, a patient weighing 46 kg may have height less than 150 cm. In such an instance, the patient's weight may correlate with the "small adult" pad set 120 and the patient's height may correlate with the "X-small Adult" pad set 120. As such, the system 340 may be of significant help to the clinician in resolving the disagreement and selecting a pad set 120.

Although not shown, the system 340 may include separate pad set correlation tables for male and female patients. In some instances, typical parameter value ranges for male patients may differ from typical parameter value ranges for female patients.

FIG. 5 illustrates a screen shot of an exemplary thermal pad set recommendation form (form) 510, in accordance with some embodiments. The form 510 includes patient parameters for which patient values may be acquired from the EMR 321. Such parameters may include the patient's gender, the patient's weight, the patient's height, and the patient's body fat percentage. The form 510 may also facilitate direct input of other patient parameter values by the clinician via the clinician device 310. These other parameters may include the patient's pant waist size, the patient's pant inseam size, and the patient's shoe size.

In some instances, the patient's pant waist size may more accurately correlate with the width 222 of the torso pads 121, 122 than the patient's weight. As such, in some instances when available, it may be advantageous to determine a pad set 120 in accordance with the patient's pant waist size. Similarly, the patient's pant inseam size may more accurately correlate with the length 221 of the thigh pads 123, 124 than the patient's height. As such, in some instances when available, it may be advantageous to determine a pad set 120 in accordance with the patient's pant inseam size.

The system 340 may display the recommended pad set 120 and an availability status on the clinician device 310. The system 340 may also display an alternative recommended pad set 120 if the recommended pad set 120 is unavailable in inventory. In some embodiments, the system 340 may display the recommended pad set, availability status, and an alternative recommended pad set 120 as a portion of the form 510.

Figure 6:
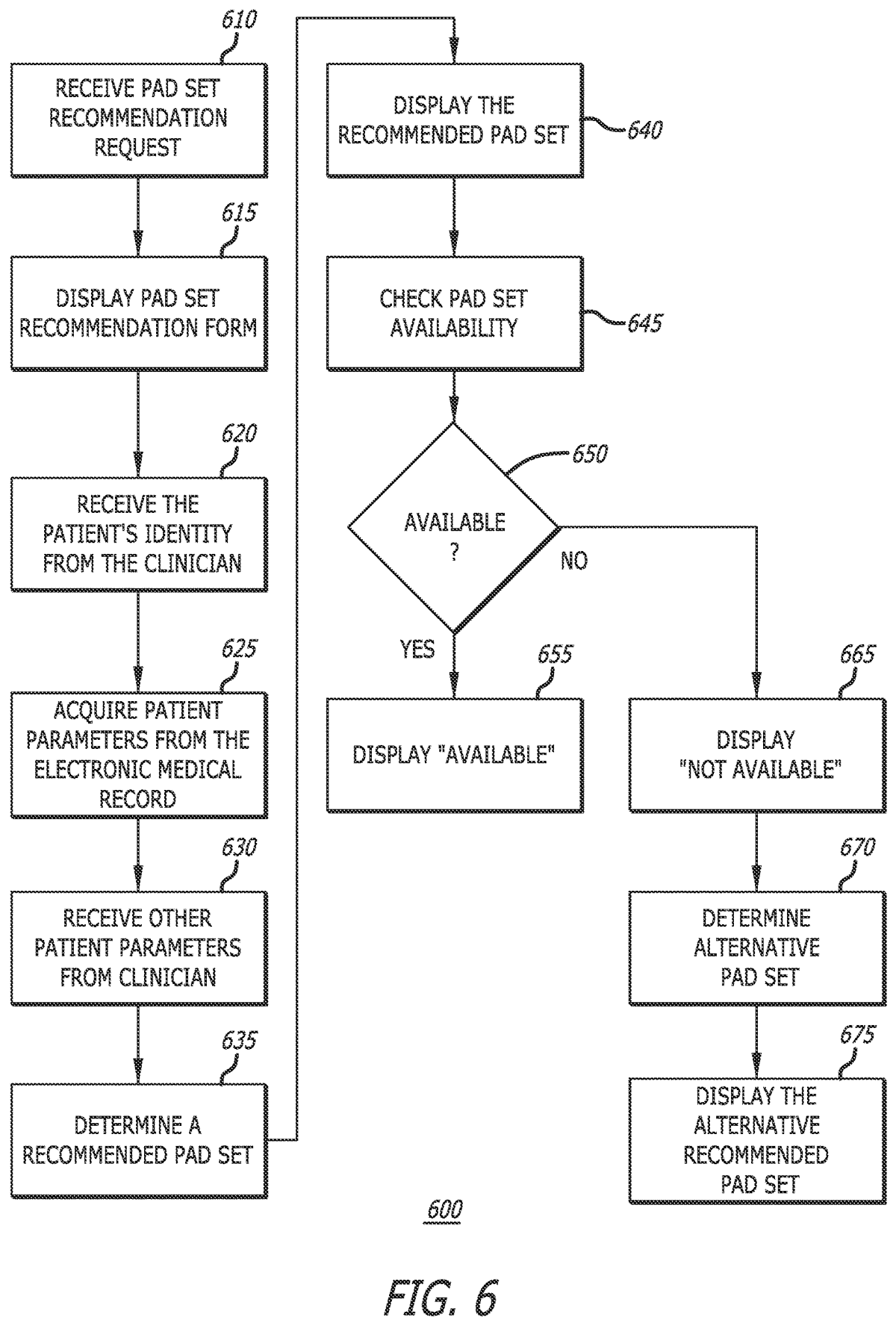

FIG. 6 illustrates a computer aided process 600 that may include the steps as described below. The logic 352 may receive a thermal pad recommendation request from the client 310 (step 610). In response, the logic 352 may display the form 510 so that the clinician 310 may input the patient's identity (step 615). The logic 352 may receive the patient's identity (e.g., the patient's name) as input by the clinician 310 (step 620). Having the patient's identity, the logic 352 may access the EMR system 320 and acquire any patient parameter values available on the patient's EMR 321 (step 625). The logic 352 may also receive any other patient parameter values as may be input by the clinician via the clinician device 310 (step 630). Having all available patient parameter values, the logic 352 may determine the recommended pad set 120 in accordance with the available patient parameter values (step 635) as further described below. Once the recommended pad set 120 is determined, the logic 352 may display the recommended pad set 120 on the clinician device 310 (step 640). The logic 352 may access the facility inventory system to determine if the recommended pad set 120 is available in inventory (step 645). If the recommended pad set 120 is available (step 650), the logic 352 may display a message accordingly (step 655).

If the recommended pad set 120 is not available (step 650), the logic 352 may display a message that the recommend pad set 120 is not available (step 665). The logic 352 may then determine an alternative pad set 120 from the pad sets 120 available in inventory (step 670) and display the alternative recommended pad set 120 on the clinician device 310 (step 675).

The determining step 635 may include operations as performed by the pad set determining logic 352. The logic 352 may determine the recommended pad set 120 from available patient parameter values on the form 510. In some instances, one or more patient parameter values may be omitted from the form 510, in which instances, the logic 352 may provide a recommended pad set 120 from the available patient parameter values on the form 510. In some embodiments, one patient parameter may provide a more accurate correlation to the pad set 120 than another patient parameter. For example, the patient's pant waist size may represent a patient's torso circumference more accurately than the patient's weight and thus may correlate more accurately to the pad set 120 than the patient's weight. In some instances, the patient's weight may correlate with a pad set 120 that is different (e.g., smaller or larger) than the pad set 120 that correlates with the patient's height. In some embodiments, the logic may apply a greater correlation significance to one patient parameter over another patient parameter. For example, in some embodiments, the logic 352 may apply a greater correlation significance to the patient's pant waist size and the pant inseam size, since the dimensions associated with these patient parameters may align more accurately with the dimensions of the pads, i.e., the length 221 and the width 222 (see FIG. 2).

In some instances, a patient parameter value may be close to an end of the parameter value range such that either of two pad sets 120 may equally correlate with the patient parameter value. In such an instance, the logic 352 may utilize a value of another patient parameter to determine which of the two pad sets 120 may define a better fit with the patient 50.

In some embodiments, the logic 352 may sequentially refine the pad set recommendation in accordance with ordered patient parameters. For example, the logic 352 may initially determine a recommended pad set 120 in accordance with a first patient parameter, (e.g., the patient's weight). Thereafter, the logic 352 may refine or alter the pad set recommendation in accordance with a second patient parameter, (e.g., the patient's height). Thereafter, the logic 352 may further refine or alter the pad set recommendation in accordance with a third patient parameter, (e.g., the patient's pant waste size). This pattern of refinement may continue until each of the available patient parameters have been used in determining the recommended pad set 120.

In some embodiments, the logic 352 may initially determine a recommended pad set 120 in accordance with a first set of patient parameters, (e.g., the patient parameters available from the EMR). Thereafter, the logic 352 may refine or alter the pad set recommendation in accordance with a second set of patient parameter, (e.g., the patient parameters input directly into the form 510 by the clinician).

A few examples of the pad set determining step 635 describe exemplary operations (e.g., algorithmic operations) of the logic 352, in accordance with some embodiments.

Example 1. The patient has a weight of 84 kg and a height of 185 cm. All other patient parameter values may be omitted on the form 510. In this example, the patient's weight is in the middle of the weight range for the "Large Adult" pad set 120, and the patient's height is in the middle of the height range for the "Large Adult" pad set 120. In response, the logic 352 may determine that the patient parameter values correlate with the "Large Adult" pad set 120.

Example 2. The patient has weight of 44 kg and a height of 160 cm. All other patient parameter values may be omitted on the form 510. In this example, the patient's weight is at the high end of the weight range for the "X-Small Adult" pad set 120, and the patient's height is at the high end of the height range for the "Small Adult" pad set 120. In response, the logic 352 may determine that patient parameter values correlate more accurately with the "Small Adult" pad set 120 over the "X-Small Adult" pad set 120 since using the "Small Adult" pad set 120 may provide sufficient length for the patient and the extra width may result in acceptable pad overlap.

Example 3. The patient has weight of 74 kg and a height of 150 cm. All other patient parameter values may be omitted on the form 510. In this example, the patient's weight is at the high end of the weight range for the "Medium Adult" pad set 120, and the patient's height is in the middle of the height range for the "Small Adult" pad set 120. In response, the logic 352 may determine that patient parameter values correlate more accurately with the "Medium Adult" pad set 120 over the "Small Adult" pad set 120 since using the "Medium Adult" pad set 120 may provide sufficient width to extend around the torso and thighs of the patient and the extra length of the thigh pads may acceptably extend into the knees of the patient and the extra length of torso pads may acceptably extend down to the hips of the patient.

Example 4. The patient has weight of 58 kg, a height of 155 cm, a pant waist size of 72 cm, and a pant inseam size of 70 cm. In this example, the patient's weight is at the high end of the weight range for the "Small Adult" pad set 120, the patient's height is in the middle of the height range for the "Small Adult" pad set 120, the patient's waist size is at the low end of the waist range for the "Medium Adult" pad set 120, and the patient's inseam is in the middle of the inseam range for the "Small Adult" pad set 120. In response, the logic 352 may determine that patient parameter values correlate more accurately with the "Medium Adult" pad set 120 over the "Small Adult" pad set 120 since the patient's waist size is a more accurate indication of the torso circumference than the patient's weight.

Example 5. The patient has weight of 74 kg, a height of 175 cm, a pant waist size of 75 cm, and a pant inseam size of 87 cm. In this example, the patient's weight is at the high end of the weight range for the "Medium Adult" pad set 120, the patient's height is at the high end of the height range for the "Medium Adult" pad set 120, the patient's waist size is in the middle of the waist range for the "Medium Adult" pad set 120, and the patient's inseam is in the middle of the inseam range for the "Large Adult" pad set 120. In response, the logic 352 may determine that patient parameter values correlate more accurately with the "Large Adult" pad set 120 since the patient's inseam is a more accurate indication of the thigh length than the patient's height.

Example 6. The patient has weight of 44 kg and a height of 160 cm. All other patient parameter values may be omitted on the form 510. In this example, the patient's weight is at the high end of the weight range for the "X-Small Adult" pad set 120, and the patient's height is at the high end of the height range for the "Small Adult" pad set 120. In response, the logic 352 may determine that patient parameter values correlate more accurately with the "Small Adult" pad set 120 over the "X-Small Adult" pad set 120 since using the "Small Adult" pad set 120 may provide sufficient length for the patient and the extra width may result in acceptable pad overlap. However, in this example, the logic 352 determines that the "Small Adult" pad set 120 is not available in inventory. As such, the logic 352 may define the "X-Small Adult" pad set 120 as the alternative pad set recommendation.

Example 7. Each of the height, weight and body fat percentage of the patient are unknown. However, a clinician is able to determine the size of the patient's waist via a pant waist size and the patient's shoe size. In the scenario in which the patient's pant waist size is 40 cm and has a shoe range of 6 (US children's size), the logic 352, upon receipt of such information, determines that a "Large Child" pad set 120 is appropriate. Here, the logic 352 determines the pant size corresponds to the "Large Child" pad set 120 and the shoe size corresponds to a "Medium Child" pad set 120. As a result, the logic 352 recommends the larger pad size.

Example 8. The patient has a weight of 100 kg and a height 150 cm. In this example, the patient's weight is at the high end of the weight range for the "Large Adult" pad set 120 and the patient's height is at the high end of the height range for the "X-Small Adult" pad set 120. However, in this situation, the logic 352 may recommend the "X-Large Adult" pad set 120. Such a recommendation may be based on experiential data that is included within the logic 352. In some embodiments, the logic 352 may include a trained machine learning model that provides a scoring of thermal pad set sizes based on input parameters disclosed above, where training is performed utilizing training data (e.g., scores of how a particular thermal pad set size fits on a patient, e.g., provided by clinicians).

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Embodiments of the invention may also relate to an apparatus for performing the operations herein. This apparatus may be specially constructed for the required purposes, and/or it may include a general-purpose computing device selectively activated or reconfigured by a computer program stored in the computer. Such a computer program may be stored in a tangible computer readable storage medium or any type of media suitable for storing electronic instructions, and coupled to a computer system bus. Furthermore, any computing systems referred to in the specification may include a single processor or may be architectures employing multiple processor designs for increased computing capability.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A system comprising:

one or more processors;

a non-transitory computer-readable medium communicatively coupled to the one or more processors and having instructions stored thereon that, when executed by the one or more processors, cause performance of operations including:

receiving a request for a thermal pad set recommendation for use with an identified patient from a clinician device, accessing an electronic medical record (EMR) for the identified patient, retrieving values for a first set of patient parameters for the identified patient from the EMR, determining the thermal pad set recommendation according to the values for the first set of patient parameters in combination with a pad set correlation table, and displaying the thermal pad set recommendation on the clinician device; and a thermal contact pad set configured for application to a patient undergoing a targeted temperature management (TTM) therapy and corresponding to the thermal pad set recommendation including at least one of a torso pad chosen from a plurality of torso pads having different dimensions or a thigh pad chosen from a plurality of thigh pads having different dimensions wherein the TTM therapy includes circulating a TTM fluid through the at least one of the torso pad or the thigh pad.

2. The system of claim 1, wherein the thermal contact pad set comprises at least one torso pad and at least one thigh pad.

3. The system of claim 1, wherein the thermal contact pad set comprises at least more than one thigh pad or more than one torso pad.

4. The system of claim 1, wherein the first set of patient parameters comprises a weight of the patient and a height of the patient.

5. The system of claim 4, wherein the first set of patient parameters further comprises a gender of the patient or a body fat percentage of the patient.

6. The system of claim 1, wherein the operations further comprise receiving values for a second set of patient parameters from the clinician device.

7. The system of claim 6, wherein the second set of patient parameters comprises at least one of a pant waist size, a pant inseam size, or a shoe size of the identified patient.

8. The system of claim 6, wherein the second set of patient parameters comprises at least two of a pant waist size, a pant inseam size, or a shoe size of the identified patient.

9. The system of claim 7, wherein determining the thermal pad set recommendation comprises:

determining an initial pad set recommendation for use with the identified patient in accordance with values of a third set of patient parameters;

refining the thermal pad set recommendation in accordance with values of a fourth set of patient parameters in combination with the values of the third set of patient parameters, and wherein rendering the thermal pad set recommendation on the clinician device comprises rendering the refined thermal pad set recommendation.

10. The system of claim 9, wherein the refined thermal pad set recommendation is different from the initial pad set recommendation.

11. The system of claim 9, wherein the third set of patient parameters comprises one or more of the first set of patient parameters, and wherein the fourth set of patient parameters comprises one or more of the second set of patient parameters.

12. The system of claim 9, wherein the third set of patient parameters comprises a weight and/or a height of the identified patient.

13. The system of claim 9, wherein the fourth set of patient parameters comprises a pant waist size and/or a pant inseam size of the identified patient.

14. The system of claim 1, wherein the operations further comprise:

accessing a facility inventory system; and determining an availability of the thermal pad set recommendation in inventory.

15. The system of claim 14, wherein if the thermal contact pad set is not available in inventory, the operations further comprise:

determining an alternative pad set; and displaying the alternative pad set on the clinician device.

16. The system of claim 1, wherein determining the thermal pad set recommendation according to the values of a first set of patient parameters is performed using a trained machine learning model, wherein the trained machine learning model receives as input one or more patient parameter values and provides one or more resultant scores.

17. The system of claim 16, wherein a highest resultant score is provided as a recommended thermal pad set.

18. The system of claim 9, wherein values for the first set of patient parameters are retrieved from the EMR.

* * * * *